United States Patent
Hall et al.

(10) Patent No.: US 11,555,763 B2
(45) Date of Patent: Jan. 17, 2023

(54) TOILET EQUIPPED TO PROVIDE FECAL ANALYSIS

(71) Applicant: Hall Labs, LLC, Provo, UT (US)

(72) Inventors: David R. Hall, Provo, UT (US); David Crismon, Herriman, UT (US); Joshua Larsen, Spanish Fark, UT (US); K. Jeffrey Campbell, Spanish Fork, UT (US); Jared Reynolds, Spanish Fork, UT (US); Jared Blake, Provo, UT (US)

(73) Assignee: Medic, Inc., Provo, UT (US)

( * ) Notice: Subject to any disclaimer, the term of this patent is extended or adjusted under 35 U.S.C. 154(b) by 393 days.

(21) Appl. No.: 16/744,854

(22) Filed: Jan. 16, 2020

(65) Prior Publication Data
US 2020/0225121 A1    Jul. 16, 2020

Related U.S. Application Data

(60) Provisional application No. 62/793,002, filed on Jan. 16, 2019.

(51) Int. Cl.
| | |
|---|---|
| *G01N 1/04* | (2006.01) |
| *G01N 1/44* | (2006.01) |
| *G01N 1/28* | (2006.01) |
| *E03D 11/13* | (2006.01) |
| *A61B 10/00* | (2006.01) |
| *G01N 33/483* | (2006.01) |

(52) U.S. Cl.
CPC .......... *G01N 1/04* (2013.01); *A61B 10/0038* (2013.01); *E03D 11/13* (2013.01); *G01N 1/286* (2013.01); *G01N 1/44* (2013.01); *G01N 33/4833* (2013.01); *G01N 2001/2873* (2013.01)

(58) Field of Classification Search
CPC ............ G01N 1/04; G01N 1/286; G01N 1/44; G01N 33/4833; G01N 2001/2873; A61B 10/0038; E03D 11/13
See application file for complete search history.

(56) References Cited

U.S. PATENT DOCUMENTS

2018/0271501 A1*  9/2018  Wang ..................... G01G 19/00

* cited by examiner

*Primary Examiner* — Nicole M Ippolito (57) ABSTRACT

A toilet is disclosed. The toilet has a bowl adapted to receive excreta, a shelf for receiving feces in the bowl, and one or more sensor for detecting a property of the feces. The property may be related to a user's heath and wellness and may be presented to a person for their review and assessment.

20 Claims, 11 Drawing Sheets

FIG. 12

TOILET EQUIPPED TO PROVIDE FECAL ANALYSIS

CROSS-REFERENCE TO RELATED APPLICATIONS

This application claims priority to U.S. Provisional Application No. 62/793,002 filed on Jan. 16, 2019, which is incorporated herein by reference in its entirety.

TECHNICAL FIELD

The present disclosure relates to smart toilets. More particularly, it relates to smart toilets equipped to provide health and wellness information about a user.

BACKGROUND

The ability to track an individual's health and wellness is currently limited by the lack of available data related to personal health. Many diagnostic tools are based on examination and testing of excreta, but the high cost of frequent doctor's visits and/or scans make these options available only on a very limited and infrequent basis. Thus, they may not be widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. By the time symptoms motivate seeking care, preventative care may be eliminated as an option leaving only more intrusive and potentially less effective curative treatments. An ounce of prevention is worth a pound of cure.

Just a few examples of smart toilets and other bathroom devices can be seen in the following U.S. patents and Published applications: U.S. Pat. No. 9,867,513, entitled "Medical Toilet With User Authentication"; U.S. Pat. No. 10,123,784, entitled "In Situ Specimen Collection Receptacle In A Toilet And Being In Communication With A Spectral Analyzer"; U.S. Pat. No. 10,273,674, entitled "Toilet Bowl For Separating Fecal Matter And Urine For Collection And Analysis"; US 2016/0000378, entitled "Human Health Property Monitoring System"; US 2018/0020984, entitled "Method Of Monitoring Health While Using A Toilet"; US 2018/0055488, entitled "Toilet Volatile Organic Compound Analysis System For Urine"; US 2018/0078191, entitled "Medical Toilet For Collecting And Analyzing Multiple Metrics"; US 2018/0140284, entitled "Medical Toilet With User Customized Health Metric Validation System"; US 2018/0165417, entitled "Bathroom Telemedicine Station." The disclosures of all these patents and applications are incorporated by reference in their entireties.

SUMMARY

In a first aspect, the disclosure provides a toilet. The toilet has a bowl to receive feces and urine, a shelf within the bowl for receiving feces, and at least one sensor for detecting a property of the feces. The property of the feces is related to a user's health and wellness.

In a second aspect, the disclosure provides a method for providing user health and wellness data. The method includes providing a toilet, detecting at least one property of the feces, and providing information on the property. The toilet is like that described above. The property is detected by a sensor and made available for use.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration

DETAILED DESCRIPTION

The following description recites various aspects and embodiments of the inventions disclosed herein. No particular embodiment is intended to define the scope of the inventions. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "excreta" is meant to refer to human waste discharged from the body, especially in the form of feces and/or urine.

As used herein, "toilet" is meant to refer to any device or system for receiving human excreta, including urinals.

As used herein, the term "bowl" refers to the portion of a toilet that is designed to receive excreta.

As used herein, the term "base" refers to the portion of the toilet below and around the bowl supporting it.

As used herein, the term "user" refers to any individual who comes into contact with the toilet, including one who deposits excreta therein.

As used herein, the term "gas" refers to gas and vapors, particulate matter, and any other molecule that may be suspended in and flow with gas.

As used herein, the term "sensor" refers to anything that can detect properties in a quantitative or qualitative analysis, such as a sensor or transduce.

Exemplary Embodiments

The present disclosure relates to a toilet configured to receive excreta and detect at least one property of feces before disposing of the excreta. Preferably, this property is one which may be indicative of a user's health, especially when the reviewer is informed in health and wellness, such as a medical professional, specialist, or care giver.

In one preferred embodiment, a shelf in the toilet bowl receives the feces. While on the shelf, analysis of the feces is performed. Many forms of analysis are possible, some of which include weighing it, spectral analysis, high temperature processes such as burning with a laser, and capturing and analyzing the vapors. Once analysis of the feces on the shelf is complete, water may wash across the shelf and carry the feces to a secondary processing area. Once at the secondary processing area, a probe may be used to further process or analyze the feces, samples of the feces may be taken, the feces may be mixed with water to form a solution, one or more reagents may be added, and/or additional processing or analysis can be conducted. Finally, when the feces is no longer needed, a valve in the secondary processing area opens and the feces is flushed out of the toilet. Alternatively, analysis initiated while the feces is on one of the shelf or the secondary processing area may be sufficient and preclude the necessity of processing and/or analyzing at both the shelf and a secondary processing area.

Flushing the feces from the toilet as described above is one of many methods for disposing of excreta or human waste, some of which are mentioned below. In one preferred embodiment, the toilet disposes of the excrete into a sewer. In another embodiment, the toilet disposes of the excreta into a septic system. In an alternative embodiment, the toilet incinerates the excreta and vents the gases and vapors. In another embodiment, the excreta is dehydrated or turned into ash, following which it can be stored and collected later. Another alternative uses a combination of disposal methods to dispose of the excreta.

Figure 3:
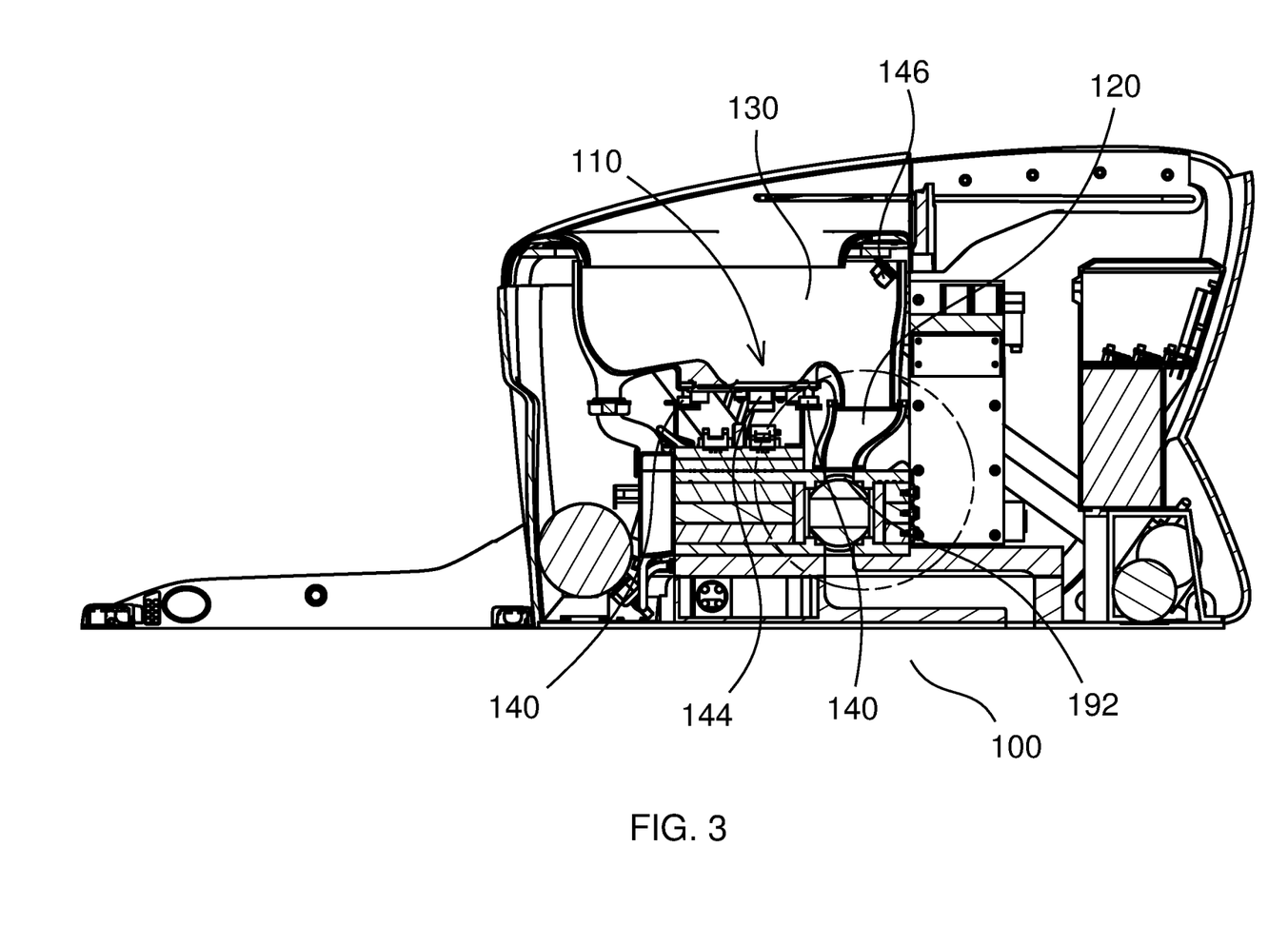
FIG. 3 is a cross section of one embodiment of the invention.

Referring to FIG. 3, in one preferred embodiment, there is a shelf 110 upon which feces is deposited within toilet 100. This shelf may be integrated into the bowl or alternatively may be separate from the bowl. Additionally, bowl 130 is configured to separate the urine from the feces so they may be analyzed separately from each other. Alternatively, a design may be selected in which the bowl does not separate the urine from the feces. Preferably, shelf 110 is integrated into bowl 130, toilet 100 is configured with at least one sensor 140 to measure the weight of bowl 130, and the weight and/or mass of the feces is determined from the measurements of the weight of bowl 130. Preferably, sensor 140 can also measure the impact force of the feces being deposited onto shelf 110 and/or into bowl 130. Some ways of measuring of the weight of the bowl include a pressure sensor, a strain gauge, and a scale. Preferably, sensor 140 measures the weight of bowl 130. Additionally, shelf 110 is configured with an optical or spectral analysis sensor 144. Preferably, optical or spectral analysis sensor 144 is positioned below shelf 110 and shelf 110 is configured with a transparent or translucent portion through which sensor 144 analyzes the feces. It is also possible an optical or spectral analysis sensor is located to the side and/or above the shelf or at other analysis areas in the toilet. Preferably, the sensor for detecting a property of the feces is attached or connected to the toilet and/or its internal component by physically mounting and/or via an electronic data connection.

In one preferred embodiment, when feces is initially deposited into the toilet, the shelf supports non-diarrhetic feces (feces that essentially comprises non-watery stools) in a manner such that the feces is not submerged. In other words, there is minimal or no standing water in contact with the portion of the shelf where feces is deposited just prior to the feces being deposited. Preferably, the initial deposit of feces is into minimal or no standing water.

In general, but especially in an embodiment where the weight of the bowl is being measured, care should be taken to isolate electronics from liquid and other damage. Care should also be taken to ensure containment of the excreta and in preserving the sterility of the sample collecting and testing environments. Additionally, care should be taken to isolate the sewer connection to prevent gasses from the sewer from entering undesirable sections of the toilet and any space in which the toilet is installed since gasses and other contaminants in sewers can compromise excreta analysis and pollute the user environment where the toilet is installed.

The shelf allows for treatment and analysis of at least a portion of the feces.

Preferably, shelf 110 is flat, approximately 3" wide by 3" long. Shelf 110 has sensor 144 positioned below the shelf and the shelf has 1-2 optically transparent or translucent portions to facilitate sensor 144 detecting at least one property of the feces on the shelf. Alternatively, the shelf is partially flat or slightly tipped from horizontal.

Moving the feces off of the shelf can be done in many ways. The selection of the method and the variables inherent to each method depend on many considerations, including what processing and analysis has already been performed, what additional processing and analysis will be performed, effectiveness of moving the feces, resource requirements (power, water, time, consumables, etc.), and effectiveness of cleaning and/or sterilizing the shelf. A selection of methods is described below. Each method can be implemented independently or as a combination of multiple methods.

As mentioned above, water can wash across the shelf to carry the feces from the shelf into the secondary processing area, such as represented by secondary processing area 120 in FIG. 3. Regarding the method of using water to move the feces, there are many important variables, including water pressure, water temperature, water volume, where the water is applied, whether to purify the water, and whether to include an additive or filter. The design of the shelf will be dependent on the method selected and may dictate factors such as how the shelf is supported, the location of the shelf in the toilet, the shape of the shelf, the material or materials from which the shelf is made, and the processes used to make and install the shelf.

The water readily available will, in many cases, be tap water. The temperature of available tap water varies greatly between 32° F. to 150° and depends factors such as time of year, whether the pipes supplying the water had a significant run underground, and if the water went through a water heater. Generally, tap water for toilets comes from underground pipes, may be temporarily stored in a reservoir within a building, and bypasses any water heaters that supply hot water. Tap water pressure can vary from ambient up to 150 psi or higher and depends on factors such as the pressure in the supply line or elevation of reservoirs, pressure regulators, head loss, and whether other valves in the system are open. City supplied residential water pressure is often around 40-60 psi and, when installed, pressure regulators often keep the incoming water at a maximum of 50 psi. In taller buildings, the water pressure to the building is insufficient to provide water where water is needed at sufficient pressures so pressure increasing systems may be used. Additionally, tap water has a varying molecular composition since water typically has naturally occurring trace minerals and various additives to control the quality of the water.

The characteristics of tap water supplied to the toilet may or may not be adequate. As such, the toilet may be configured to change the water in a variety of ways, including heating the water, cooling the water, purifying the water, electrolyzing the water, deionizing the water, adding additives to the water, increasing the pressure, decreasing the pressure. Additionally, such changes could be performed before the water enters the toilet.

Figure 7A:
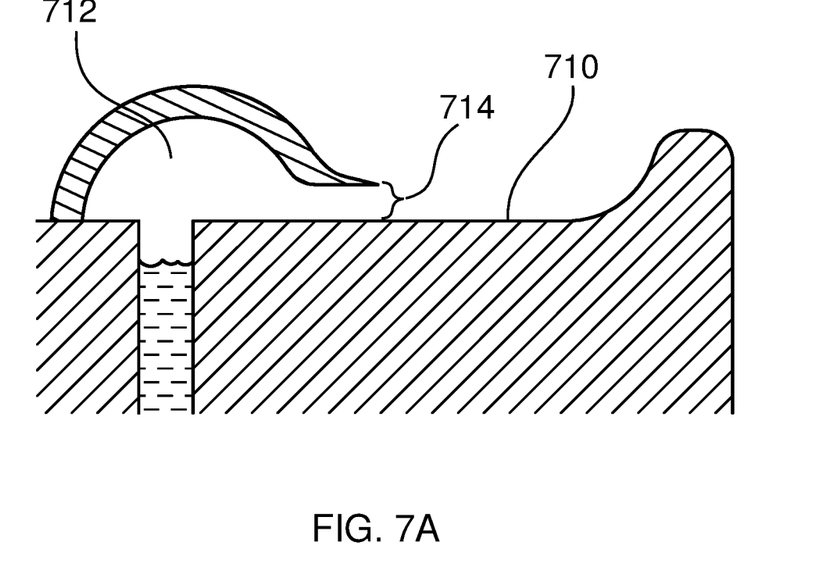
FIG. 7a is a cross section view of a portion of one embodiment of the invention.
Figure 7B:
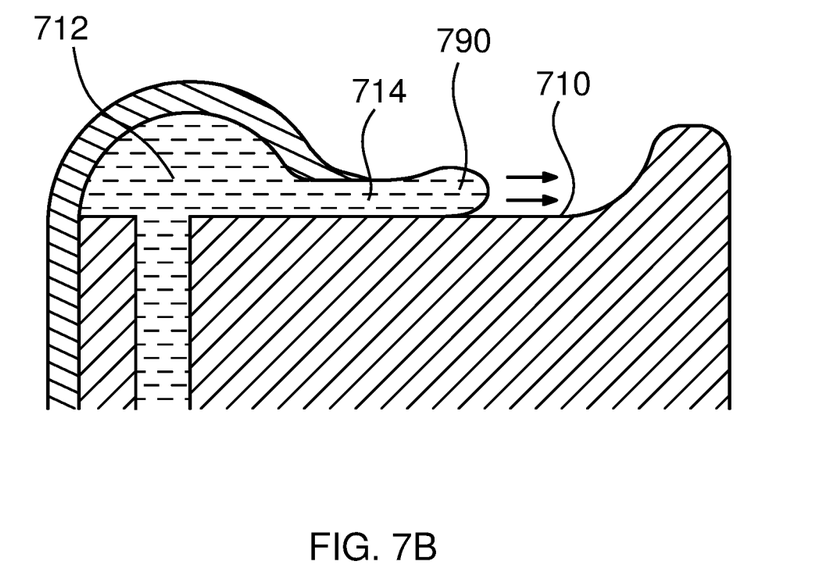
FIG. 7b is a cross section view of a portion of one embodiment of the invention.

In one preferred embodiment shown in FIGS. 7a and 7b, a volume of water may be supplied to shelf 710 via wave 790 of water. More preferably, water enters cavity 712 proximate to the shelf, wherein the cavity has an outlet 714 directing wave 790 at shelf 710 which to clean the shelf of feces. Preferably, the opening of outlet 714 is approximately ⅛"-¼" high and the width of the shelf. In one preferred embodiment, cleaning and/or sterilizing agents are added to the water to aid in cleaning and/or sterilizing the shelf.

Figure 8A:
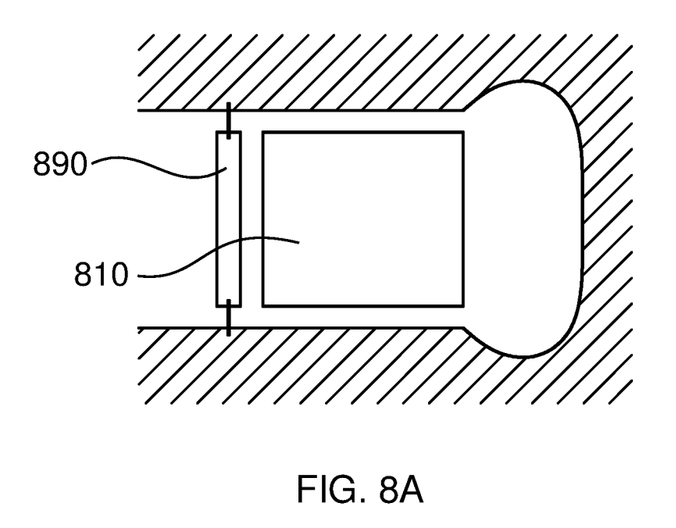
FIG. 8a is a top view of a portion of one embodiment of the invention.
Figure 8B:
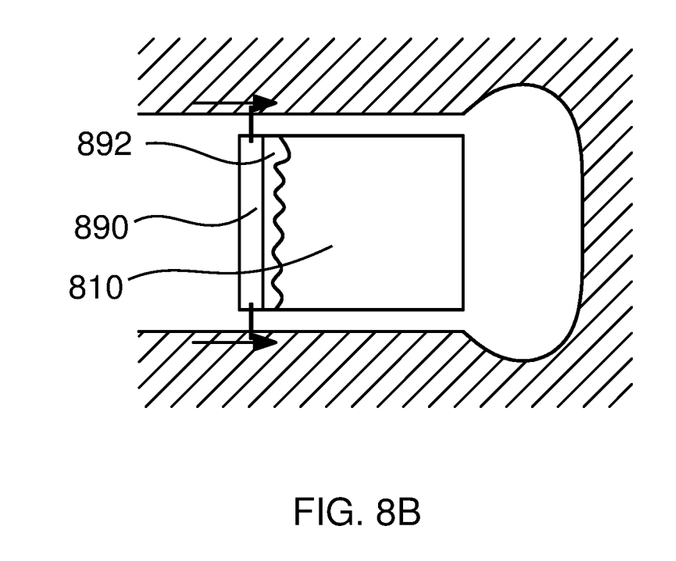
FIG. 8b is a top view of a portion of one embodiment of the invention.
Figure 8C:
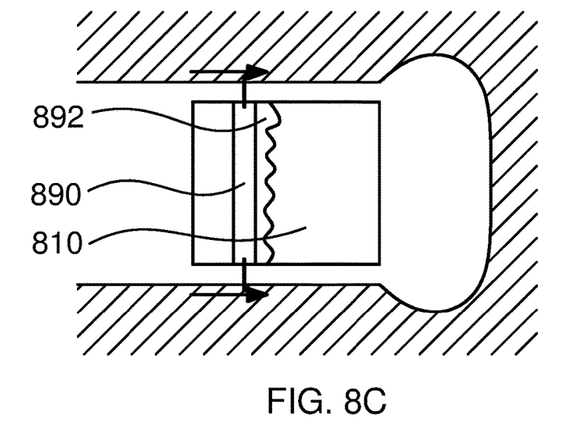
FIG. 8c is a top view of a portion of one embodiment of the invention.
Figure 8D:
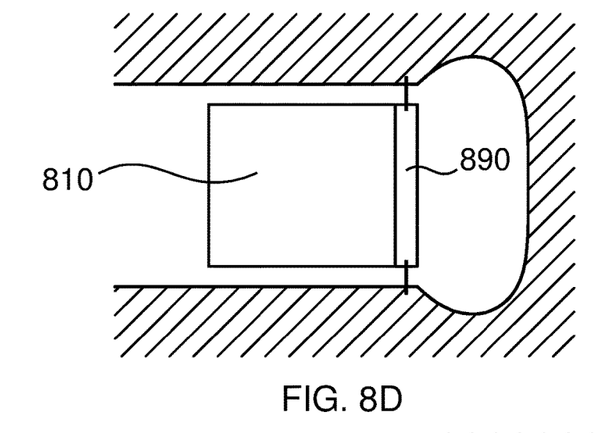
FIG. 8d is a top view of a portion of one embodiment of the invention.
Figure 8E:
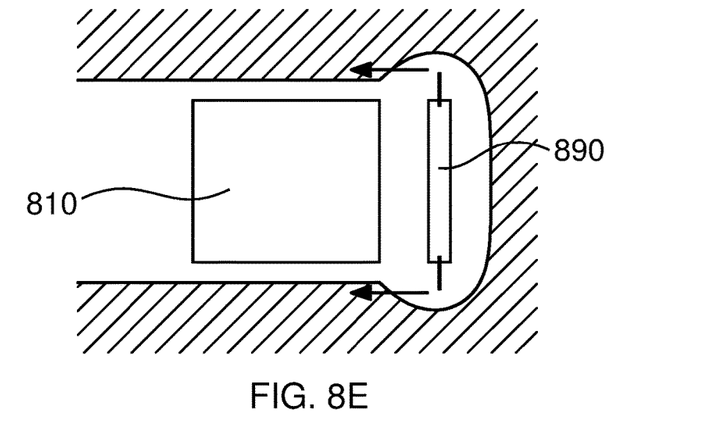
FIG. 8e is a top view of a portion of one embodiment of the invention.
Figure 9A:
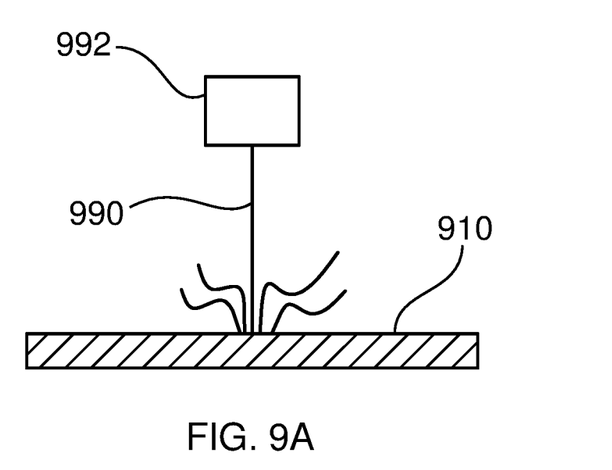
FIG. 9a is a cross section view of a portion of one embodiment of the invention.
Figure 9B:
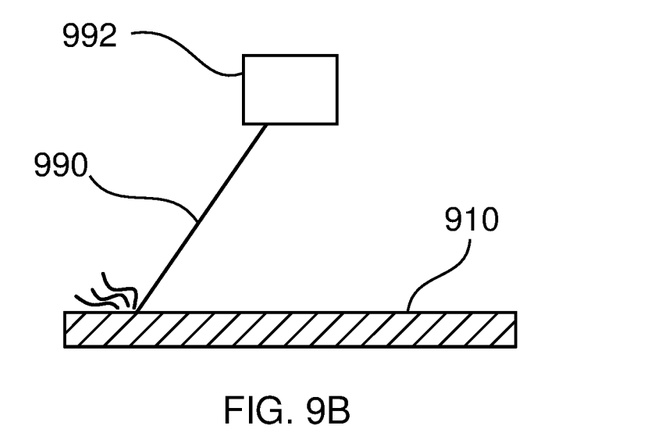
FIG. 9b is a cross section view of a portion of one embodiment of the invention.
Figure 9C:
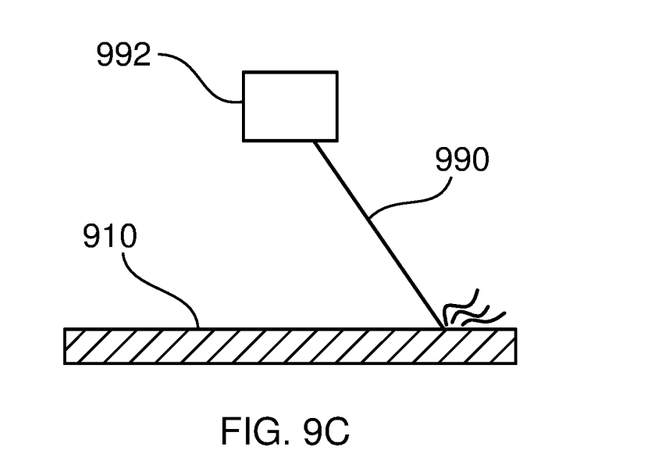
FIG. 9c is a cross section view of a portion of one embodiment of the invention.

In an alternative embodiment, there is a squeegee that wipes the shelf to remove the feces. Alternatively, one or more jet of water or a water blade is sprayed onto the shelf to remove the feces from and/or sterilize the shelf. As depicted in FIGS. 9a, 9b, and 9c, nozzle 992 supplies jet 990 and is fixed in location within the toilet. Nozzle 992 is configured to be able to change the direction of jet 990 to target specific spots on the shelf. Accompanying a directable jet would be a system for controlling the direction and a system that determines where the jet needs to be directed. In another embodiment depicted in FIGS. 8a, 8b, 8c, 8d, and 8e, squeegee 890 is configured so one or more water jet or a water blade sprays shelf 810 as squeegee 890 traverses shelf 810, creating water spray 892. The squeegee 890 may only travel the distance of the shelf 810 as depicted in FIGS. 8b, 8c, and 8d, or the squeegee 890 may also travel beyond a side of shelf 810 as depicted in FIG. 8a or 8e. Again, the water in a jet may have additives for cleaning and/or sterilizing the shelf and/or other elements of the toilet.

Figure 11:
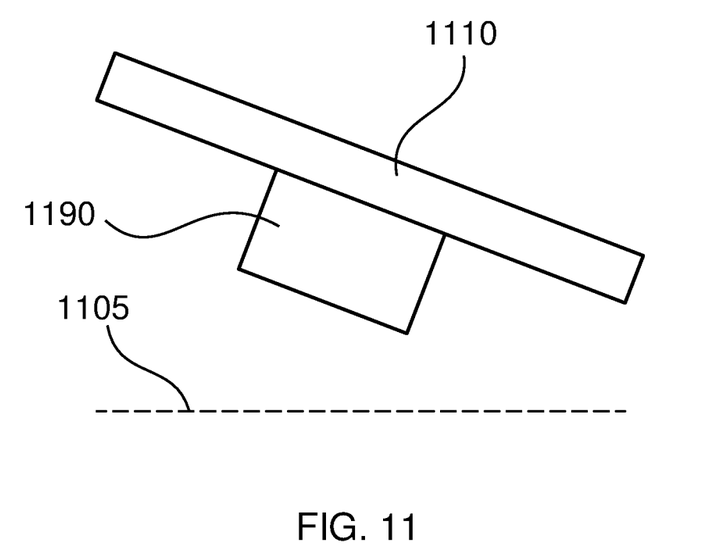
FIG. 11 is a side view of a portion of one embodiment of the invention.
Figure 12:
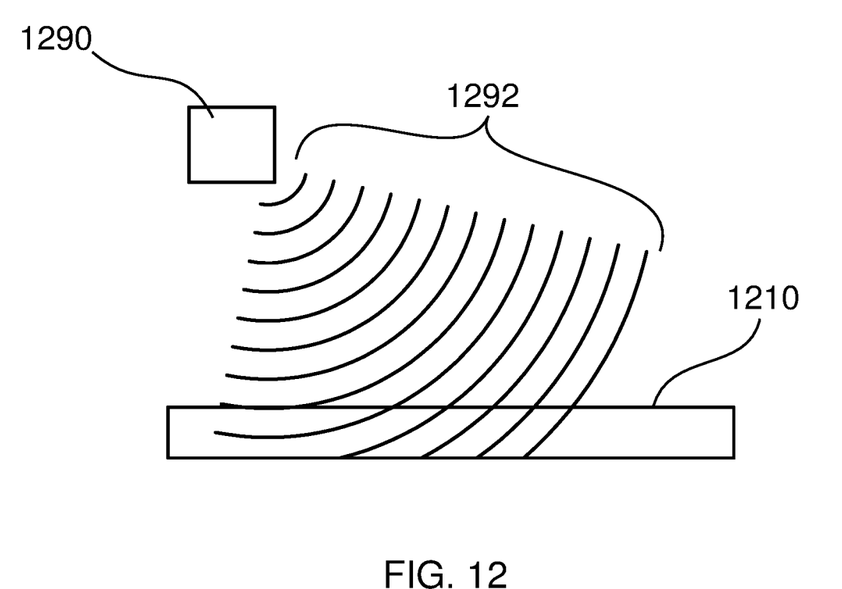
FIG. 12 is a side view of a portion of one embodiment of the invention.

In an alternatively method of moving the feces, vibration may be used to move the platform. The vibration may be applied to the feces, shelf, and or other parts of the toilet. It may come from and in many forms, including acoustic or pressure waves, impulses, vibration motors, piezoelectric devices, or sonic or ultrasonic sources. FIG. 11 depicts one embodiment wherein shelf 1110 vibrates due to vibration source 1190 attached to shelf 1110. Preferably, shelf 1110 is at an angle offset from horizontal. Alternatively, the top of the shelf has a portion which is horizontal and another portion which is not. FIG. 12 depicts an embodiment where source 1290 is mounted with in the toilet and generates pressure waves 1292 which bombard shelf 1210. Preferably, the shelf is angled so that gravity may assist in removing the feces from the shelf. Alternatively, vibration may be used to reduce excreta to a minimum thickness for analysis.

Alternatively, a heated shelf or another source of heat (such as steam) may be applied to the bottom of the feces, a result of which might be the boiling of liquid in the feces, creating a gas layer upon which the feces can float. By floating the feces on a gas layer, the friction holding the feces in place is significantly reduced, allowing the feces to move much more freely. Once in this state, if the shelf is angled, the feces could slide off of the shelf with the assistance of gravity. Also, while in this state, any portion of a force applied to the feces parallel to the shelf would have an increased effect on moving the feces. Thus, something like a small amount of air pressure or flowing water could be used to move the feces off of the shelf. Possible ways of heating include microwave radiation, piezoelectric vibration, a hot plate, laser evaporation, laser ablation, mechanical mixer, and mechanical ablation.

Figure 10A:
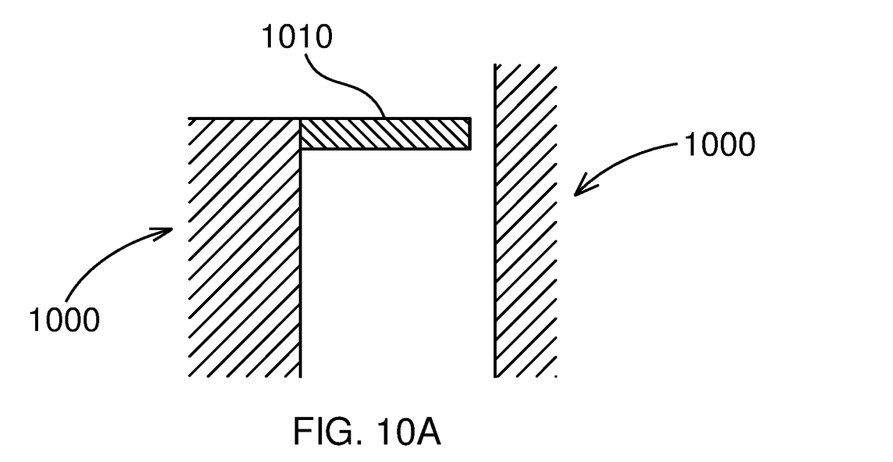
FIG. 10a is a cross section view of a portion of one embodiment of the invention.
Figure 10B:
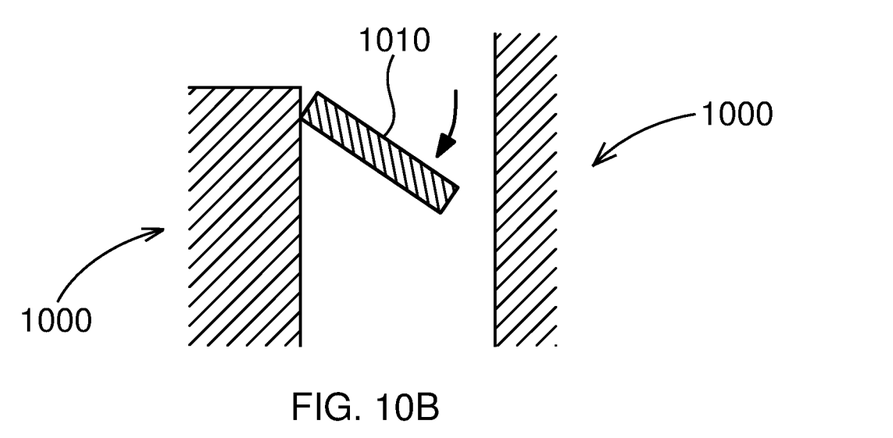
FIG. 10b is a cross section view of a portion of one embodiment of the invention.
Figure 10C:
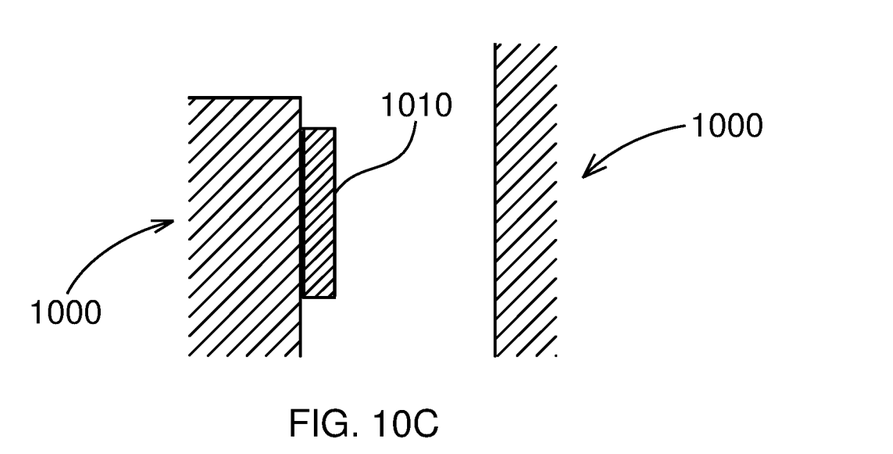
FIG. 10c is a cross section view of a portion of one embodiment of the invention.

Alternatively, in one preferred embodiment, the shelf 1010 is cantilevered from the toilet 1000 on a hinge. Based on the analysis being performed, the shelf can be selectively released so it drops from its initial horizontal orientation to an angled or vertical orientation, at which point, the feces can slide off the cantilevered shelf and into the toilet bowl. In some embodiments, the cantilever is in connection with a pressure sensor, for example a scale or strain gauge. A measurement of the weight and/or mass of the feces may be collected prior to depositing the feces into the toilet bowl. Alternatively, the shelf may have a seam, be supported by two or more hinges, and separate relative to itself as the portions angle. FIGS. 10*a*, 10*b*, and 10*c* depict a cantilevered shelf. In FIG. 10*a*, shelf 1010 is in a horizontal or near horizontal orientation and is configured to support feces. As depicted in FIGS. 10*b* and 10*c*, when the feces is no longer needed on shelf 1010, shelf 1010 can be selectively rotated from its initial horizontal position to an angled or vertical position.

Alternatively, the shelf may be pretreated to be or with a hydrophobic coating, a hydrophilic coating, and/or water.

Figure 2:
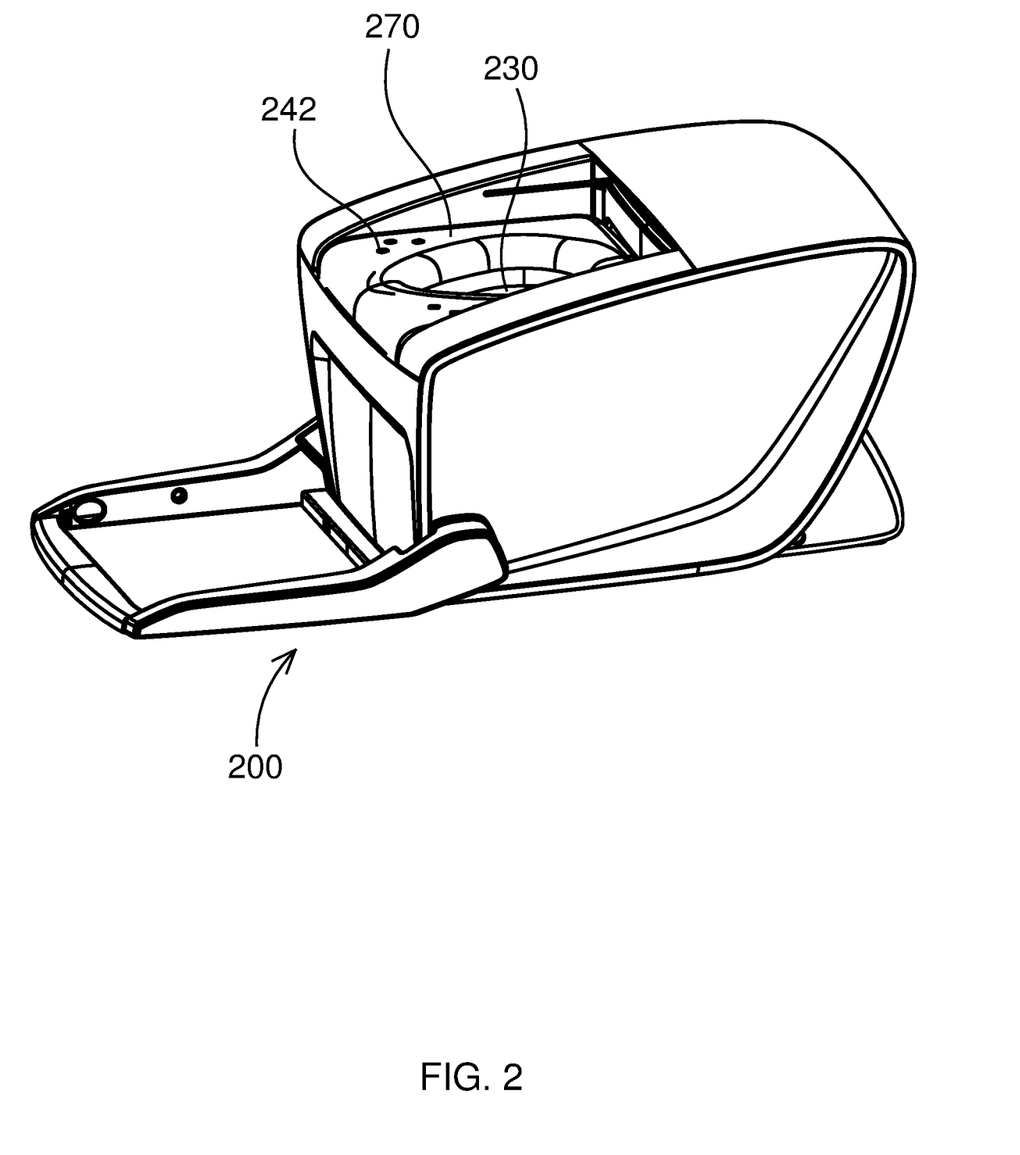
FIG. 2 is an isometric view of one embodiment of the invention.

In one embodiment, the toilet includes a lid which may be closed manually after a user finishes using the toilet. More preferably, the toilet automatically closes the lid when the toilet detects the user is no longer seated, using a proximity or other sensor 242. Sensor 242 may be in electronic communication with a controller which, in turn, sends a signal to close the lid when the sensor signals that the user has left the toilet. The controller may be connected to the lid through wires, electromagnetic waves (including infrared, visible, and ultraviolet), or other non-wired means. The lid may be in connection with a power source. Additionally, upon receiving the signal from the proximity or other sensor, the controller may initiate other cycles of the toilet, such as excreta processing, excreta analysis, excreta disposal, toilet cleaning and/or sterilizing, hibernation or other low power mode.

Figure 1:
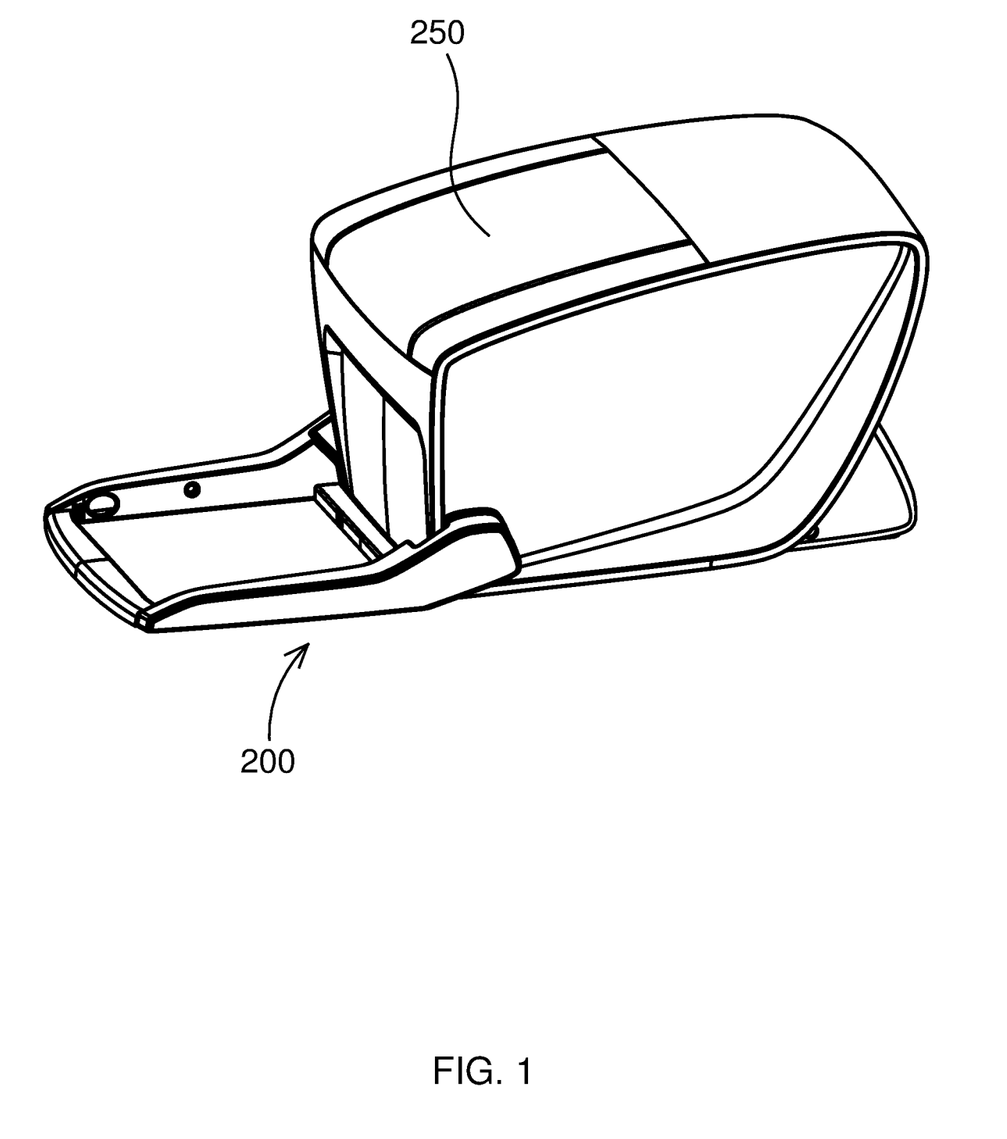
FIG. 1 is an isometric view of one embodiment of the invention.

FIGS. 1 and 2 show a preferred embodiment wherein, lid 250 has been closed and cooperates with other components of the toilet to form an air seal within toilet 200, enclosing the space within toilet bowl 230, especially the parts adapted to receive feces or urine, from the environment around the toilet to facilitate conducting analysis of the excreta. FIG. 2 shows the toilet 200 with the lid open (lid not visible because it's inside the toilet), exposing bowl 230 to the outside environment. FIG. 1 shows toilet 200 with lid 250 closed. Unlike traditional toilets, this preferred embodiment may seal the toilet, excreta processing areas, and/or excreta analysis areas from the outside environment. In one preferred embodiment, there may be a seal between lid and the toilet such that there is no air gap. To ensure a sufficient seal, a seal or gasket may be placed between lid 250 and the portions of toilet 200 that mate to the lid, which may include seat 270 and the upper rim of bowl 230. Preferably the lid, the bowl, the seat, and/or other components of the toilet creating the air seal comprise a heat resistant material capable of repeated exposure to high temperatures associated with analysis incorporating heat treatment of the excreta, burning feces for analysis, or cleansing excreta from the toilet. In some embodiments there is a seal or gasket placed between the toilet seat and the upper rim of the toilet bowl to facilitate the air seal. Preferably, the seal or gasket is also made from a heat resistant material.

Figure 4A:
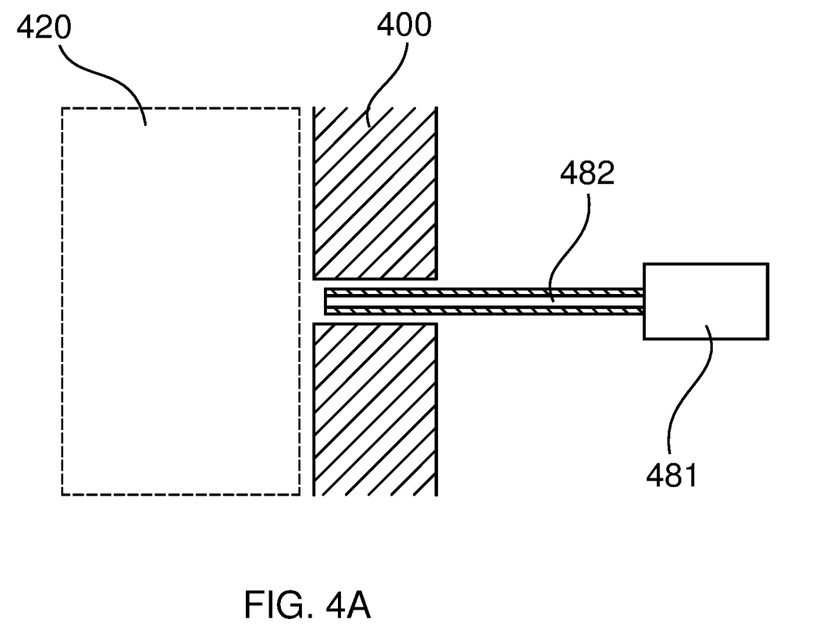
FIG. 4a is a cross section view of a portion of one embodiment of the invention.
Figure 4B:
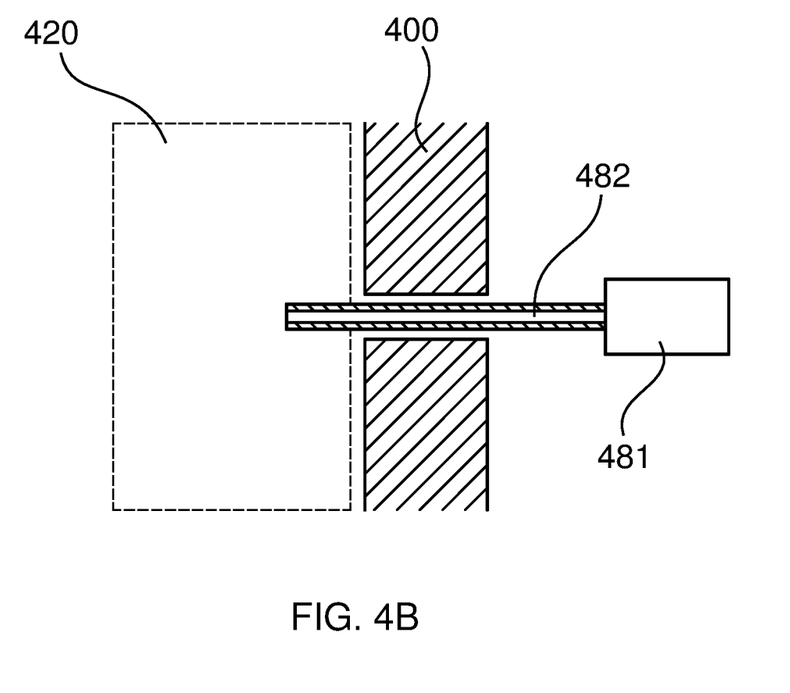
FIG. 4b is a cross section view of a portion of one embodiment of the invention.
Figure 5:
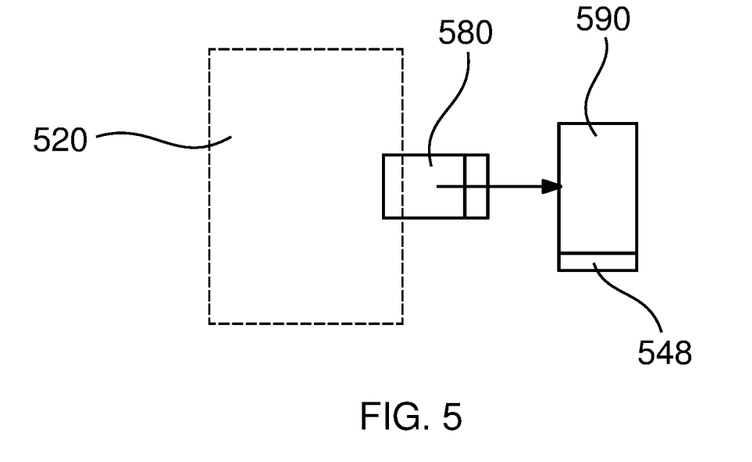
FIG. 5 is a simple diagram showing the interaction of select elements of one embodiment of the invention.

Referring to FIG. 5, in one preferred embodiment, the toiled includes a probe 580 for collecting a sample from feces. As shown in FIGS. 4*a* and 4*b*, the probe may include a needle 482 with a hollow where the sample will be received by the needle 482 that can be driven into the feces to take the sample. In this embodiment, the probe takes a sample. In an alternative embodiment, the sample may be a surface scraping from the feces.

Accompanying a hollow needle probe may also be an ejector or ejector system 481 for removing the sample from the hollow. Preferably, the ejector system 481 is air operated with the air being injected into the needle to force the sample from the needle. The air may be produced by pumping air into the needle or by pushing a plunger into a cylinder in connection with the needle similar to a plunger in a syringe of a hypodermic needle. Alternatively, a different type of pressure differential may be created to drive the sample from the needle such as with a vacuum or pushing on the sample with a plunger. Preferably, the hollow needle probe and ejector or ejector system are configured to deposit the sample into a separate testing location, such as a reaction vessel where a reagent may be added and analysis performed.

In one preferred embodiment, the toilet includes a pump to create a vacuum in the toilet bowl after the lid closes. The vacuum can pull the lid downward toward the toilet seat, applying pressure to the seal or gaskets on the top and/or bottom of the toilet seat. The result is that the toilet becomes a sealed environment within which the toilet may conduct analyses of the user's excreta.

In one preferred embodiment, the toilet includes micro capillary tubes for collecting and/or analyzing samples of excreta.

Figure 6A:
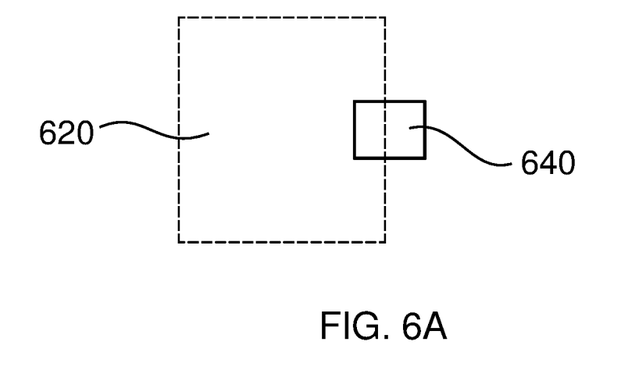
FIG. 6a is a simple diagram showing the interaction of select elements of one embodiment of the invention.
Figure 6B:
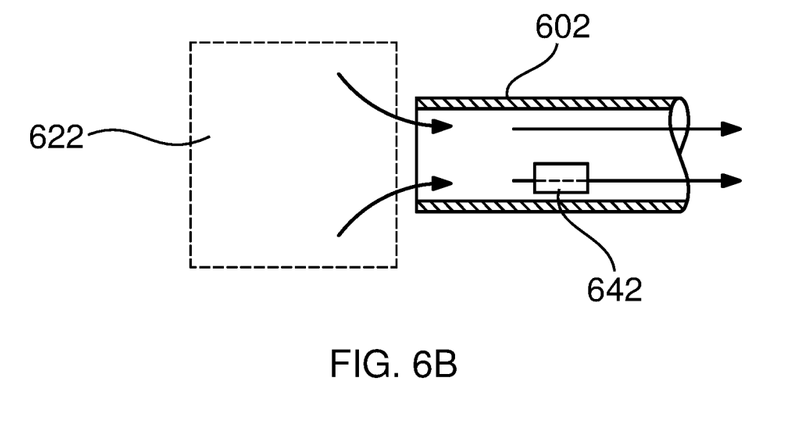
FIG. 6b is a simple diagram showing the interaction of select elements of one embodiment of the invention.

In one embodiment, a sensor detects properties of the gas in the air affected by the feces. Referring to FIG. 6*a*, in one embodiment, sensor 640 is located in contact with an air volume 620 containing the feces and can analyze the gas in the air. In an alternative embodiment shown in FIG. 6*b*, a pump within the toilet may move gas from a volume of air 622 containing the feces and to a device 602 which includes sensor 642 for analyzing the gases and vapors in the air. In a preferred embodiment, the sensor can identify and measure volatile organic compounds (VOCs) and can determine what types of VOCs are being released by the fecal matter. In one embodiment, the toilet may contain a filter to purify the air and/or capture molecules in the air for analysis. Additionally, air may be actively processed or filtered to reduce the likelihood of feces odor from reaching a user while they are using the toilet.

In one preferred embodiment, the interior of the toilet bowl may house one or more imaging sensors. The image sensors may collect images of the user's feces. In some embodiments, an imaging sensor may collect high resolution images of the feces. In some embodiments, the imaging sensors may collect microscopic images of the feces. The images may be used to assess the user's health status. Additionally, the toilet may be configured to analyze the images. In an example, the images may provide information about the shape, size, density, roughness or texture, and color of the feces. Reflective spectroscopy may also be used to assess texture and color of feces. Laser spectroscopy may also be included to analyze the feces. In one preferred embodiment, the imaging sensor detects optical electromagnetic radiation and/or another portion of the electromagnetic spectrum. Alternatively, the imaging sensors may be related to acoustic or other pressure waves. Alternatively, one or more imaging sensor is outside the bowl and the bowl has at least a portion which is a transparent or translucent medium relative to what is being detected by the imaging sensor, through which the imaging sensor and image the excreta.

In one embodiment, the bowl is made from typical toilet materials like ceramic, plastic, or metal. More preferably, the bowl is made from pressed glass or patterned glass.

In one embodiment, reagents are added to feces while it is on the shelf within the toilet bowl. To facilitate the processing and analysis, the feces may be smeared to a thin layer over a flat surface on the shelf prior to adding the reagents. A device resembling a putty knife or a blade may smear the feces and also mix the feces with the reagents by moving over the fecal sample repeatedly until the reagent and feces are sufficiently mixed. The imaging sensors may collect images of the feces after the reagent has been applied. In some embodiment, the imaging sensor may be housed within the shelf. The shelf may have an optically transparent section above the imaging sensor and the feces may be smeared over this optically transparent area. The imaging sensor may collect images of the thin layer of feces from below the optically transparent area as if it were collecting images of a smear on a glass slide. Alternatively, vibration may be used to reduce excreta to a minimum thickness for analysis.

In a preferred embodiment, the toilet includes a laser which sends a laser beam into the toilet bowl and cuts through the feces. When the cut is made, the fecal material which is internal to the fecal mass may be exposed. The one or more cameras may collect additional images of the interior of the feces. Additionally, VOCs, dioxins, particulate matter, polycyclic aromatic hydrocarbons, carbon monoxide, hexachlorobenzene, and ash may be released from the interior of the feces or created when feces is burnt. A pump may direct the VOCs, vapors, particulates, and other gasses from the process to the sensor where they may be identified and quantified and the data stored on the controller.

Laser beams of a variety of wavelengths may be used to cut through the feces. The density of the feces may be determined by assessing which wavelength best cuts through the feces. The laser beam could be applied to the feces until it is vaporized and may be disposed of in gaseous form. This same technique could vaporize urine for analysis and/or disposal.

Some analysis may have an optimal temperature. In some embodiments, the toilet bowl, other spaces within, or other elements of the toilet may be heated or cooled to conduct analytical reactions on the feces or urine that require specific temperatures. The toilet bowl could also be heated to high temperatures to dehydrate and degrade feces for easier waste processing. High heat could also be used to clean and disinfect the inside of the toilet bowl.

The toilet may include devices housed in the lid which may collect measurements which are relevant to the user's health status. In some embodiments, a device capable of performing photoacoustic imagery may be included in the lid of the toilet. This may be used to map a user's blood oxygenation, detect skin melanoma, and measure methemoglobin. In some embodiments, a device which performs acoustic analysis may be housed within the lid of the toilet. Images of a user's internal organs may be obtained using acoustic analysis while the user is seated on the toilet. In some embodiments, a stethoscope may be housed within the lid of the toilet. The user may lean back against the stethoscope in the lid while seated on the toilet. The stethoscope may be in communication with a controller which may record the sounds of the user's heartbeat and breathing as detected by the stethoscope.

VOC information and other information from user or excreta analysis may be relevant to the user's health status and may be stored on the memory of a controller which may be included within the toilet or located remotely. Camera images may be stored in a memory of the controller which may be included in the toilet or located remotely.

There are many acceptable material choices, methods of manufacture, and methods of assembly for the various parts of the toilet. The selection of materials, manufacturing processes, and assembly depends on a number of factors, including durability, expected forces, expected temperature range, aesthetics, accessibility, potential exposure to corrosive materials, ease of manufacture or assembly, cost, weight, excreta processing and analysis to be performed, ease of cleaning and sterilizing, power requirements, health and wellness assistance provisions to be incorporated, comfort, and other expected user preferences.

In one preferred embodiment, the toilet bowl, lid, valving, and other structures and mechanism are made from plastics. In another preferred embodiment, based on factors as discussed above, plastic materials are selectively exchanged with metals, ceramics, rubber, or even organic materials (such as paper) which are better suited for the application.

Referring to FIGS. 4a, 4b, and 5, in the one preferred embodiment, secondary processing area 520 is accessible by a probe 580 capable of taking a sample of the feces. More preferably, as shown in FIGS. 4a and 4b, this probe is a needle 480 with a hollow to create and hold the sample. In FIG. 4a, needle 482 is in a storage position within toilet 400. In FIG. 4b, needle 482 has extended into secondary processing area 420. After the probe receives the probe can then transfer the sample from the feces to another location for processing and analysis. For example, probe 580 may eject the sample into chamber 590 where it is mixed with water and/or a reagent, following which, sensor 548 may take readings of the mixture. Alternatively, the mixing and/or analyzing may be performed within the probe.

In another alternative embodiment, the probe comprises a mechanism 192 which actuates rotationally or laterally relative to the feces to take a slice of the feces. In another embodiment, the probe comprises an actuator that pushes the feces onto hardware that takes and/or analyses a sample of the feces.

Preferably, the toilet includes a system for sensing and/or controlling the location and orientation of the probe. Controlling the location and/or orientation of the probe may be accomplished in many ways, including the use of structures that selectively or permanently limit the probe's degrees of freedom; the use of motors, especially servomotors; the use of pneumatic or hydraulic systems; and the use of electromagnetic positioning systems. Sensing the location and/or orientation may also be accomplished in many ways, the selection of which is made based on what system—if any—is selected for controlling the location and/or orientation of the probe. Systems that sense the location and/or orientation may include a feedback system built into the motor, an optical sensor, a resistance sensor, a magnetic sensor, and a contact or other type of switch. Alternatively, the toilet may have a system that calculates the location and/or orientation of the probe through such factors as predetermined mechanical limits on the probe's motion and inputs given to the hardware controlling the location and/or orientation.

Location and/or orientation information about the probe may be used to limit or control what functions of the toilet may be allowed. For example, if the system determines that the probe has not returned to its non-use position, this information may be used to prevent the toilet from flushing. Similarly, the toilet may include other means of detecting or calculating its own state, the state of feces within the toilet, and/or the state of urine within the toilet and use these states to control functions of the toilet. In one embodiment, the function of using these states to control the functions of the toilet is especially critical in cleansing the portions of the toilet that receive, process, and/or analyze excreta to prevent contamination of the excreta and help ensure the integrity of the analyses. For example, if the toilet detects the presence of feces on the shelf during what might otherwise be the end of a flush or cleaning phase, the toilet may extend the cleaning phase and take extra steps to clean the shelf, such as applying more water or burning of the feces with high temperature.

There are many ways to analyze the excreta, which can largely be categorized by whether or not the toilet additionally processes it. For example, analysis such as weighing, optical analysis, spectrometry, and durometer testing can be performed in place without moving or dissecting the excreta. For analyses which require the use of consumables (such as adding a reagent to a feces or urine solution), a small portion of the excreta may be taken to lower the amount of consumable and or time required to receive data; this improves the appeal of the toilet as an excrement testing system through improvements such as lowering start-up and operational costs, reducing the time required between uses, extending time between maintenance events (such as refilling consumables), and saving space. As such, other analyses can involve additional processing or manipulating of the excreta, such as dividing or removing a portion of feces or urine from itself, mixing excreta to create a solution, burning or vaporizing excreta, pressing feces, and/or dehydrating excreta. Each analysis that is possible for the toilet to perform includes inherent methods, structures, and equipment that enable the completion of the analysis, creation of data, recording and storing the data, and outputting the data in a usable form. These methods, structures, and equipment, whether preexisting or invented for this toilet, are configured especially for the toilet regardless of any broader or alternative applications. In one embodiment, the toilet is configured with internal digital storage memory where analysis data on one or more feces property may be stored. In one embodiment, the toilet may be configured to export the analysis data to electronic hardware located exterior to the toilet; this data export may be a wired connection, a wireless connection using electromagnetic radiation, or even pressure waves (audible or inaudible). In one embodiment, analysis data may be presented to a person via a display built-in to the toilet. In another embodiment, analysis data may be processed and/or summarized before being presented.

In a preferred embodiment, the feces is deposited into water where it may be mixed and/or dissolved to a relatively homogenous solution. Reagents may then be added to the solution which may indicate the composition of the feces. Examples of reagents include: a biological stain; a colorimetric reagent including Coomassie Brilliant Blue G-250 dye to identify the amount of protein in the solution; Oil red-O to detect lipid in the solution; reagents used in colorimetric assay or those which may result in a product that can be detected using spectroscopy at other wavelengths, such as ultraviolet, infrared, or near infrared; reagents that can produce a fluorescent signal upon interaction with components of the feces, which signal could be detected using a device included in the toilet.

One property that can be determined is the energy with which excreta is deposited in the toilet. If a user is sitting on the toilet seat, this could provide an estimate of the force a user exerted to expel the excreta from their body.

FIGS. 1, 2, and 3 show embodiments of a toilet that depict a platform to receive a user's feet extending from the base. Analysis of the feet may then be conducted by sensors on or with a line of sight to the platform. The types of sensor can include any of those discussed above. More preferably, the sensors are imaging sensors and weight sensors. Additionally, the platform is connected to a motor and can be raised up.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. A toilet comprising:
   a bowl adapted to receive feces and urine;
   a shelf in the bowl for receiving at least a portion of the feces;
   at least one sensor for detecting a property of the at least a portion of the feces on the shelf, wherein the property is related to a user's health and wellness; and
   a removal mechanism for removing a majority of the feces, urine, or a combination thereof from the bowl;
   wherein the at least one sensor analyzes gas from the toilet and detects at least one of volatile organic compounds, vapor content, dioxins, particulate matter, polycyclic aromatic hydrocarbons, carbon monoxide, hexachlorobenzene, and ash.

2. The toilet of claim 1 wherein the at least one sensor detects one property selected from the group consisting of the force exerted by the feces, the weight of the feces, and the mass of the feces.

3. The toilet of claim 1 wherein the at least one sensor is an imaging sensor or a laser spectroscope.

4. The toilet of claim 1 further comprising a lid capable of closing, further comprising other toilet components, and wherein the closed lid cooperates with the other toilet components to form an air seal for the portion of the toilet containing the portion of the bowl adapted to receive feces and urine.

5. The toilet of claim 4 wherein the lid or other toilet components engaged in creating the air seal comprise heat resistant material.

6. The toilet of claim 1 further comprising a heat treatment applied to the feces and a system for capturing gasses released while applying the heat treatment to the feces.

7. The toilet of claim 6 wherein the heat treatment comprises a laser beam directed at the feces.

8. The toilet of claim 1 further comprising a system for removing contaminates from one or more area in which excreta is processed and/or analyzed in the toilet, wherein the system is selected from a group consisting of a source of heat, a force exerted by water, cleaning additives added to water, and sterilizing additives added to water.

9. The toilet of claim 1 wherein the removal mechanism comprises at least one selection from the group containing a volume of water, a cleaning additive in a volume of water, a sterilizing additive in a volume of water, a wave of water, and a selectively directable jet of water.

10. The toilet of claim 1 wherein the removal mechanism comprises at least one of the group containing a squeegee that wipes feces from the shelf, a mechanism that pushes the feces, a mechanism attached to the shelf which vibrates the shelf, a piezoelectric device, pressure waves bombarding the feces, and a top of the shelf with a permanent non-horizontal angle.

11. The toilet of claim 1 wherein the removal mechanism comprises a mechanism for selectively angling the shelf from an initial horizontal or near horizontal orientation.

12. The toilet of claim 1 wherein the removal mechanism comprises a heat source capable of heating the shelf or heating the bottom of the feces.

13. The toilet of claim 1 further comprising a secondary processing location within the toilet and wherein part of the at least a portion of feces is moved from the shelf to the secondary processing location to undergo one or more processes in preparation for detecting a property of the feces.

14. The toilet of claim 1 further comprising a probe for collecting a sample from the feces.

15. The toilet of claim 14 wherein the probe comprises a hollow within a needle to collect the sample and the toilet further comprises an ejection system for removing the sample from the hollow of the needle.

16. The toilet of claim 14 wherein the probe comprises a slicing mechanism to cut the feces.

17. The toilet of claim 1 further comprising a lid, wherein the lid comprises sensors for collecting measurements from a user while the user is seated on the toilet.

18. A method for providing user health and wellness data comprising:
   providing a toilet comprising:
      a bowl adapted to receive feces and urine;
      a shelf in the bowl for receiving at least a portion of the feces;
      at least one sensor for detecting a property of the at least a portion of the feces on the shelf, wherein the property is related to a user's health and wellness;
      a removal mechanism for removing a majority of the feces, urine, or a combination thereof from the bowl; and
   wherein the at least one sensor analyzes gas from the toilet and detects at least one of volatile organic compounds, vapor content, dioxins, particulate matter, polycyclic aromatic hydrocarbons, carbon monoxide, hexachlorobenzene, and ash;
   detecting at least one property of the feces using the at least one sensor; and
   providing information on the at least one property from the user's feces.

19. The method of claim 18 further comprising the step of transmitting the at least one property from the user's feces as data to a hardware outside of the toilet.

20. A toilet comprising:
   a bowl adapted to receive feces and urine;
   a shelf in the bowl for receiving at least a portion of the feces;
   at least one sensor for detecting a property of the at least a portion of the feces on the shelf, wherein the property is related to a user's health and wellness; and
   a removal mechanism for removing a majority of the feces, urine, or a combination thereof from the bowl; and
   a lid capable of closing, further comprising other toilet components, and wherein the closed lid cooperates with the other toilet components to form an air seal for the portion of the toilet containing the portion of the bowl adapted to receive feces and urine.

* * * * *